United States Patent
Stebbins et al.

(10) Patent No.: US 10,520,437 B1
(45) Date of Patent: Dec. 31, 2019

(54) HIGH SENSITIVITY SENSOR UTILIZING ULTRA-FAST LASER PULSE EXCITATION AND TIME DELAYED DETECTOR

(71) Applicant: RAYTHEON COMPANY, Waltham, MA (US)

(72) Inventors: Adriane Stebbins, Cardiff, CA (US); Kalin Spariosu, Thousand Oaks, CA (US); Lacy G. Cook, El Segundo, CA (US)

(73) Assignee: RAYTHEON COMPANY, Waltham, MA (US)

( * ) Notice: Subject to any disclaimer, the term of this patent is extended or adjusted under 35 U.S.C. 154(b) by 0 days.

(21) Appl. No.: 16/421,702

(22) Filed: May 24, 2019

(51) Int. Cl.
| | |
|---|---|
| *G01J 3/30* | (2006.01) |
| *G01N 21/64* | (2006.01) |
| *G01N 33/53* | (2006.01) |

(52) U.S. Cl.
CPC ..... *G01N 21/6458* (2013.01); *G01N 21/6428* (2013.01); *G01N 33/5308* (2013.01); *G01N 2021/6439* (2013.01)

(58) Field of Classification Search
CPC .......... G01N 21/6458; G01N 21/6428; G01N 33/5308; G01N 2021/6439; G01N 21/47; G02B 13/14; G02B 3/04; G02B 25/00; G02B 27/10; G02B 27/42; G02B 3/00
See application file for complete search history.

(56) References Cited

U.S. PATENT DOCUMENTS

| | | | |
|---|---|---|---|
| 5,592,320 A | * | 1/1997 | Wissinger ............ H04B 10/118 398/121 |
| 6,017,696 A | | 1/2000 | Heller |
| 6,048,690 A | | 4/2000 | Heller |
| 6,403,367 B1 | | 6/2002 | Cheng et al. |
| 8,063,386 B2 | | 11/2011 | Yekta et al. |
| 8,194,126 B2 | | 6/2012 | David et al. |
| 9,347,742 B2 | | 5/2016 | Varshneya et al. |
| 2006/0147927 A1 | | 7/2006 | Geddes et al. |
| 2006/0263777 A1 | | 11/2006 | Tong |

OTHER PUBLICATIONS

Avery Sonnenberg, et al.; Rapid Electrokinetic Isolation of Cancer-Related Circulating Cell-Free DNA Directly from Blood; Clinical Chemistry 60:3 (2014); pp. 500-509, Cancer Diagnostics.

Avery Sonnenberg, et al.; Dielectrophoretic isolation and detection of cancer-related circulating cell-free DNA biomarkers from blood and plasma; Electrophoresis 2014, Wiley-VCH Verlag GmbH & Co. KGaA, Weinheim; pp. 1-9.

Jean M. Lewis, et al.; Detecting cancer biomarkers in blood: challenges for new molecular diagnostic and point-of-care tests using cell-free nucleic acids; Expert Review; Expert Rev. Mol. Diagn. Early online, 1-14 (2015).

(Continued)

*Primary Examiner* — Abdullahi Nur
(74) *Attorney, Agent, or Firm* — Cantor Colburn LLP

(57) ABSTRACT

A system for imaging a biological target includes a light excitation source providing an excitation laser pulse. The system also includes an objective lens that receives reflections of the excitation laser pulse. The system further includes a reimaging optical lens that generates an image of an entrance pupil of the objective lens. The system includes a time-delayed detector that detects the image of the entrance pupil.

20 Claims, 6 Drawing Sheets

(56) References Cited

OTHER PUBLICATIONS

Stuart D. Ibsen, et al.; Rapid Isolation and Detection of Exosomes and Associated Biomarkers from Plasma; ACS Nano; Jun. 19, 2017; pp. A-K.
Stuart D. Ibsen, et al.; Recovery of Drug Delivery Nanoparticles from Human Plasma using an Electrokinetic Platform Technology; HHS Public Access; Published Small. Oct. 2015 ; 11(38): 5088-5096. doi:10.1002/smll.201500892; pp. 1-18.

\* cited by examiner

HIGH SENSITIVITY SENSOR UTILIZING ULTRA-FAST LASER PULSE EXCITATION AND TIME DELAYED DETECTOR

BACKGROUND

The present disclosure relates in general to high sensitivity sensors, and more specifically, to high sensitivity sensors utilizing ultra-fast laser pulse excitations and time delayed detectors combined with pupil plane integrated signal detection for signal-to-noise (SNR) enhancement.

Fluorescence detection is a technique that analyzes fluorescence from a sample. A beam of light, such as from a lamp, a laser, or a light-emitting diode (LED), excites electrons in molecules of certain compounds and causes them to fluoresce or emit light, which is typically, but not necessarily, visible light. The emitted fluorescent light reaches a detector, which can be placed at 90° to the incident light beam to minimize the risk of transmitted or reflected incident light reaching the detector. The detector can either be single-channeled, which detects intensity one wavelength at a time, or multi-channeled, which detects the intensity of all wavelengths simultaneously. At low concentrations, the fluorescence intensity will generally be proportional to the concentration of the fluorophore.

Fluorescence detection offers one of the most sensitive methods for quantification of probe molecules in biological and material systems. Consequently, this technique is widely used in the assaying of biochemical and cellular samples.

SUMMARY

According to embodiments of the present invention, a system for imaging a biological target includes a light excitation source providing an excitation laser pulse. The system also includes an objective lens that receives reflections of the excitation laser pulse. The system further includes a reimaging optical lens that generates an image of an entrance pupil of the objective lens. The system includes a time-delayed detector that detects the image of the entrance pupil.

According to other embodiments of the present invention, a system for imaging a biological target includes a light excitation source providing an excitation laser pulse. The system also includes a total internal reflectance microscope objective lens. The system further includes an objective lens that receives reflections of the excitation laser pulse. The system includes a reimaging optical lens that generates an image of an entrance pupil of the objective lens. The system further includes a time-delayed detector that detects the image of the entrance pupil.

According to some embodiments of the present invention, a method for imaging a biological target includes providing an excitation laser pulse to the biological target. The method includes receiving, by an objective lens, reflections of the excitation laser pulse from the biological target. The method further includes generating an image, by a reimaging optical lens, of an entrance pupil image of the objective lens. The method further includes detecting by a detector, following a time delay, the entrance pupil image.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Figure 1:
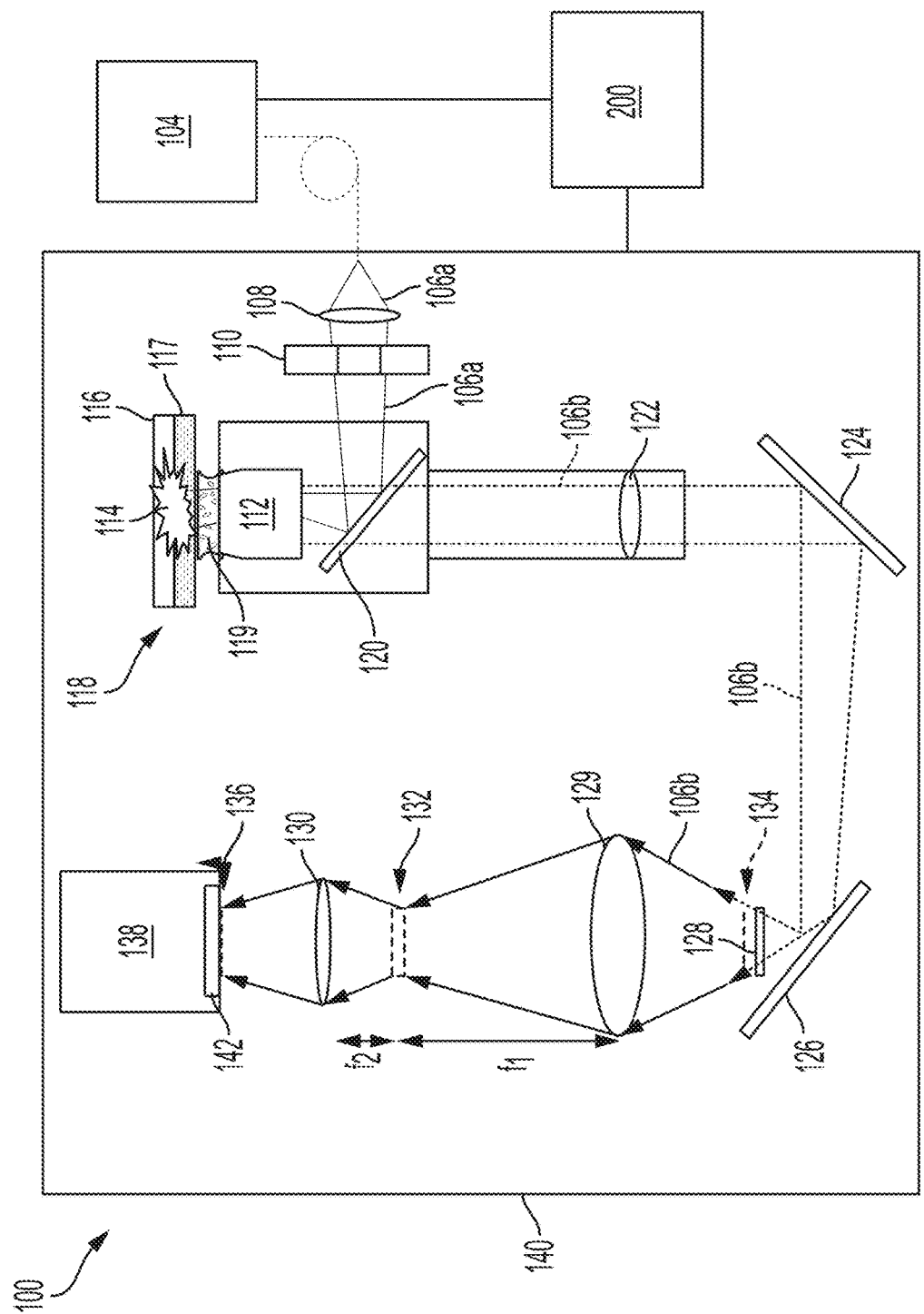
FIG. 1 illustrates a diagram of a system according to embodiments of the present invention.

Turning now to an overview of technologies that are more specifically relevant to aspects of the invention, the ability to analyze biological material using fluorescence detection is limited due to several challenges. First, portable sensors for detecting biological material, such as deoxyribonucleic acid (DNA) and ribonucleic acid (RNA), are practically limited due to the need to perform wet chemistry and other processes in the fluidic form. For example, even technology that enables biological agents, such as DNA and RNA, to be isolated from blood requires wet-based polymerase chain reaction (PCR) to amplify the DNA or RNA, which is cumbersome and time-consuming.

Second, attainment of high sensitivity levels in fluorescence detection requires rejection of noise from background light. The greatest source of background noise is from arises from the scattering of the excitation light (e.g., white light or light-emitting diode (LED)), which overlaps temporarily with the detection sensor system. Even when highly sensitive detectors capable of single photon counting are used, such as complementary metal oxide semiconductor (CMOS) cameras, the best sensitivity attainable is on the order of ~100,000 photons for the desired signal-to-noise ratio, even with narrow emission fluorescence band pass filters. These challenges prohibit the ability to detect fluorescently tagged biological agents that may be present in numbers as low as ten to several hundred.

Various approaches have been used to address the above challenges. For example, optical filters, or excitation light rejection techniques, which employ narrow band fluorescent filters have been used. However, in the case of broad spectral band white light excitation, noise from the leakage of side band filters can still obscure the detected emission fluorescence. More recently, fiber optic coupled LEDs have been utilized instead of mercury white lamp sources. However, these excitation sources also can give rise to substantial off resonance emissions that again contribute to noise and obscure the emission fluorescence signal.

Turning now to an overview of the aspects of the invention, one or more embodiments of the invention address the above-described shortcomings of the prior art by providing methods and systems that include ultra-fast pulsed laser sources that enable pulsed excitation of fluorophores in biological samples of interest. The lasers have sufficient intensity levels that can readily be frequency doubled or tripled for visible wavelength excitation. Subsequent fluorescence is detected with a time delayed and/or triggered sensor cameras. The optical box, including the detector, sample, and related optics, are sealed in a housing from outside light. The systems include an optical train that places the detector imager in the pupil plane for spatially integrated signal detection.

The above-described aspects of the invention address the shortcomings of the prior art by using methods and systems with high sensitivity and eliminate the need for spectral filters, as well as afford high sensitivity detection that eliminates the need for amplification of biological agents, such as by PCR. The systems and methods enable single photon detection of fluorescently tagged biological agents. The systems and methods can be used in portable, field-deployable sensor applications.

Turning now to a more detailed description of aspects of the present invention, FIG. 1 illustrates a diagram of a system 100 according to embodiments of the present invention. The system 100 includes a light source 104 to excite a target sample 118 with a fluorescent (or fluorescently stained, tagged, or labeled) component, and a detector 138 to detect fluorescent emissions from the target sample 118. The system 100 can include other components that ordinarily be found in fluorescent microscopes, which will be described in more detail. For a number of the components there are multiple potential embodiments, which depend upon the target application.

The light source 104 (also referred to as a light excitation source) is a laser that outputs an excitation beam 106a as an excitation laser pulse with an excitation wavelength to the target sample 118. The light source 104 can include or more lasers. According to embodiments of the present invention, the light source 104 is a telecommunications grade ultra-fast pulsed laser source with a high bandwidth (e.g., up to tens of GHz, or the digital data rate of Giga Bits per second. Basically, one GHz ($10^9$ Hz) translates to a one nanosecond (ns) pulse duration, and tens of GHz translates to ~10-100s of picoseconds (ps) pulse durations, which is important in temporally "gating out" the excitation from the subsequent delayed fluorescent emission (see FIG. 3, discussed below).

Non-limiting examples of light sources 104 include ultra-high bandwidth telecom 1550 nanometer (nm) diode lasers with subsequent frequency doubling and/or tripling to generate visible light excitation pulses in the ~400-800 nm wavelength range, which is commensurate with absorption lines of various fluorophore tags. The light source 104 has low average power, which can be about 100 mW with about 100 W to about kW of peak power per pulse according to some embodiments of the present invention.

According to one or more embodiments of the present invention, the excitation beam 106a emitted from the light source have a fundamental frequency or wavelength from about 900 nm to about 1650 nm, which is about 450 to about 800 nm when frequency doubled.

According to one or more embodiments of the present invention, the fundamental laser emission of the light source 104 laser is non-linearly optically converted to near-IR or visible wavelengths to match absorption visible fluorescent dyes or fluorophores. For example, a fundamental 1.5 micrometer laser beam can be frequency doubled or tripled by non-linear optical conversion. The laser beam from the light source 104 can be optically converted to near-IR wavelengths (i.e., about 0.4 to about 0.8 micrometers), or visible wavelengths (i.e., about 400 to about 800 nanometers), according to some embodiments of the present invention.

The excitation beam 106a or excitation laser pulse from the light source 104 is appropriately shaped by passing a beam shaper 108. The beam shaper 108 shapes the excitation beam 106a before passing through the aperture stop 110, which determines the amount of light that reaches the imaging area. The excitation beam 106a is reflected off the beam splitter or filter 120 and through microscope objective lens 112 to the target sample 118.

According to some embodiments of the present invention, the microscope housing the microscope objective lens 112 is a total internal reflection (TIR) microscope, and the microscope objective lens 112 is a TIR objective lens. TIR microscopes enable observation of a thin region of a specimen, and will be described in further detail below with respect to FIG. 5. Using a TIR microscope provides various advantages. Briefly, fluorophores bound to a sample surface are in equilibrium with those in the surrounding medium. When these molecules are excited and detected with a conventional fluorescence microscope, the resulting fluorescence from fluorophores bound to the sample surface can be overwhelmed by the background fluorescence due to the much larger population of non-bound molecules. TIR microscopy allows for selective excitation of the surface-bound fluorophores within a thin region of the sample, while non-bound molecules are not excited and do not fluoresce.

The target sample 118 includes a biological sample with fluorophores 114 adhered to a surface 116 in an aqueous solution layer 116, with a glass coverslip 117 disposed thereon. An oil 119 matching the index of the glass coverslip 117 is between the microscope objective lens 112 and the glass coverslip 117. The fluorophore 114 is excited by the excitation beam 106a and emits fluorescent light 106b back through the objective lens 112, beam splitter 120, and tube lens 122. The fluorescent light 106b is reflected off folding mirrors 124, 126 (or filter units) arranged at oblique angles with respect to the emitted fluorescent light 106b.

The reflected fluorescent light 106b (also referred to as reflections of the excitation laser pulse) passes through the filter 128 arranged at the pupil entrance 134. The filter 128 is also referred to as the object and is the pupil size defined by the optical collection telescope/eye piece. The pupil size is defined by the power and placement of the two lenses. According to one or more embodiments of the present invention, the filter 128 (or the object) is the fluorophore sample and approximately 1 cm by 1 cm square.

The fluorescent light 106b then enters objective lens 129 that collects the reflected laser light from the entrance pupil 134 and focuses an image of the target sample at its focal point 132. A field stop (not shown) can be arranged at a distance away from the objective lens 129 that is equivalent to the focal length $f_1$ of the objective lens 129. The field stop can minimize the amount of stray light from around the target that is collected into the imaged signals. From this focal point 132, the light then diverges and is collected by reimaging optical lens 130. Reimaging optical lens 130 is illustrated as a single lens positioned a distance away from the focal point 132 equivalent to the lens's focal length $f_2$. However, the reimaging optical lens 130 need not be composed of a single lens, but instead can include a combination of lenses and/or optical elements. The reimaging optical lens 130 generates an image of the entrance pupil 134 of the objective lens 129. The output of the reimaging optical lens 130 is sent to the signal detector 138 arranged at the pupil plane 136 as an inverted and de-magnified image of the light entering the pupil of the objective lens 129. Utilizing the described optical relay system enables collection of all the emitted photons from the target sample 118.

Because the detector 138 is imaging the light entering the pupil itself, instead of the focused image of the target spot (at the focal length $f_1$ from the objective lens 129), this configuration is employing what is referred to as a "pupil plane imaging." Pupil plane imaging enables spatial integration of the camera pixels or elements in order to achieve square root of pixel counts, which are in the multiple millions. Generally, the SNR scales or increases with the square root of the number of additive signal samples. For example, a single image or signal sample includes associated noise. The noise decreases, or the SNR increases, with the square root of the number of additional samples collected. Placing the camera in the pupil plane ensures all photons are captured and pixels can be integrated, since not imaging, for a significant SNR. The spatially integrated detection arrangement enables high sensitivity detection of fluorescently tagged biological agents, for example, with numbers less than one hundred in some embodiments of the present invention, which eliminates the need for wet chemistry PCR amplification processes.

The detector 138 is a CMOS detector or camera that is capable of detecting the fluorescent light and generating an image. CMOS cameras include amplifiers that convert the photodiode and charge into voltage. The incident fluorescent light 106b is converted into electrical charge and then voltage for each pixel, and the voltage for each output is by sequentially switching the switches. The CMOS camera is an ultra-high sensitivity camera that implements an optical relay system that collects all the emitted photons from a sample chip.

A non-limiting example of a CMOS camera for use in embodiments of the present invention is an ORCA-flash 4.0 V2 Digital CMOS camera C11440-22CU by Hamamatsu, which includes 2048(H)×2048(V) pixels; a 6.5 µm×6.5 µm cell size; 13.312 mm×13.312 mm effective area; 30000 electron full well capacity; and 30 frames per second frame rate at full resolution.

Gating of the camera collection of the image sample is timed to coincide with fluorescence emission onset, after the delay from the laser excitation pulse. However, such gating can be achieved at the native frame rate for the camera, for example, about 30 frames per second at full resolution.

All of the optical elements, including the detector 138, optical train for pupil plane imaging (i.e., the objective lens 130 and reimaging optical lens 130), microscope objective lens 112, and target sample 118, are arranged within an enclosure 140 (also referred to as a housing) that is protected from any outside light. The enclosure 140 is a box or other container that is impervious to outside light, which mitigates noise from background light.

The detector 138 can be in one of two states and can include a shutter that opens and closes. During an "on" state, the detector 138 receives incoming light, whereas during an "off" the detector 138 does not receive incoming light. In particular, a shutter 142 of the detector 138 is open during the "on" state and closed during the "off" state. The term "activated" is used herein to refer to the detector 138 being in the "on" state, whereas the term "deactivated" is used herein to refer to the detector 138 being in the "off" state. The detector 138 can be "triggered" by the controller 200 to be activated (by opening the shutter 142) after a time delay, which obviates the need for a narrow band spectral filter. According to some embodiments of the present invention, the controller 200 activates the time-delayed detector 138 after the light source 104 has been deactivated. The shutter 142 of the detector 138 can be auto-gated, or automatically opened and closed, according to the intensity of light received. Auto-gating blocks exposure of the detector 138 to excessive light, and has no direct connection to active transmission of pulses, their timing, or their gating.

Figure 2:
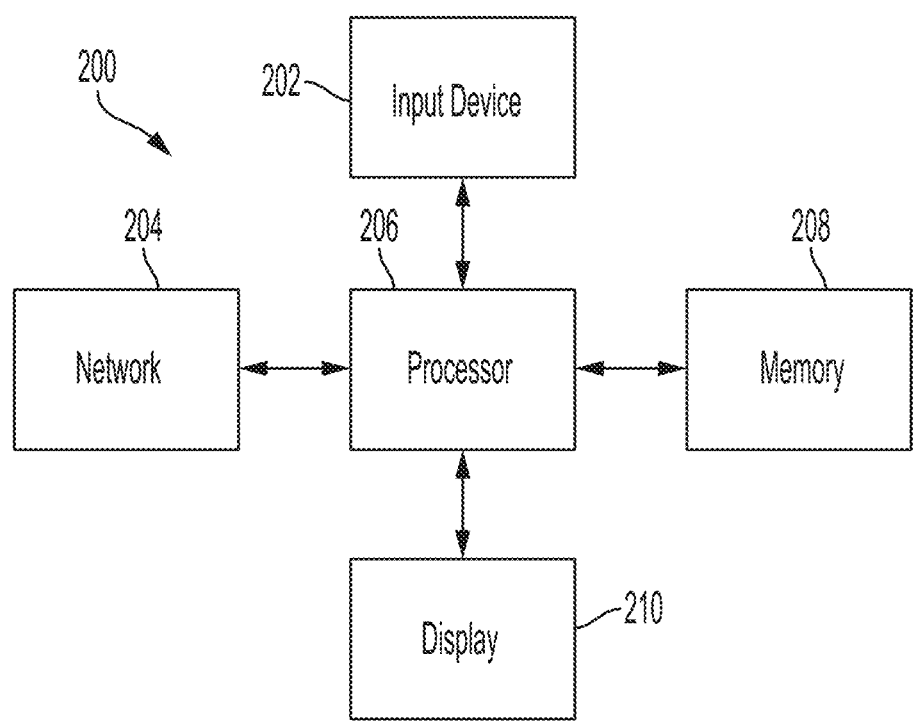
FIG. 2 illustrates a diagram of a controller for controlling a system according to embodiments of the present invention.

The system 200 is controlled by a controller 200, which is described in further detail in FIG. 2. As shown in FIG. 2, the controller 200 includes a processor 206 that is communicatively connected to an input device 202, a network 204, a memory 208, and a display 210. In the illustrated exemplary embodiment, the input device 202 can include a keyboard, touchpad, mouse, or touch screen device, and the network 204 can include a local area network or the Internet. The display 210 can include a screen, touch screen device or digital display. The display 210 displays the image received from the detector 138. In some embodiments of the present invention, the controller 200 can include a personal computer, smart phone or tablet device communicatively connected to the system 100.

Figure 3:
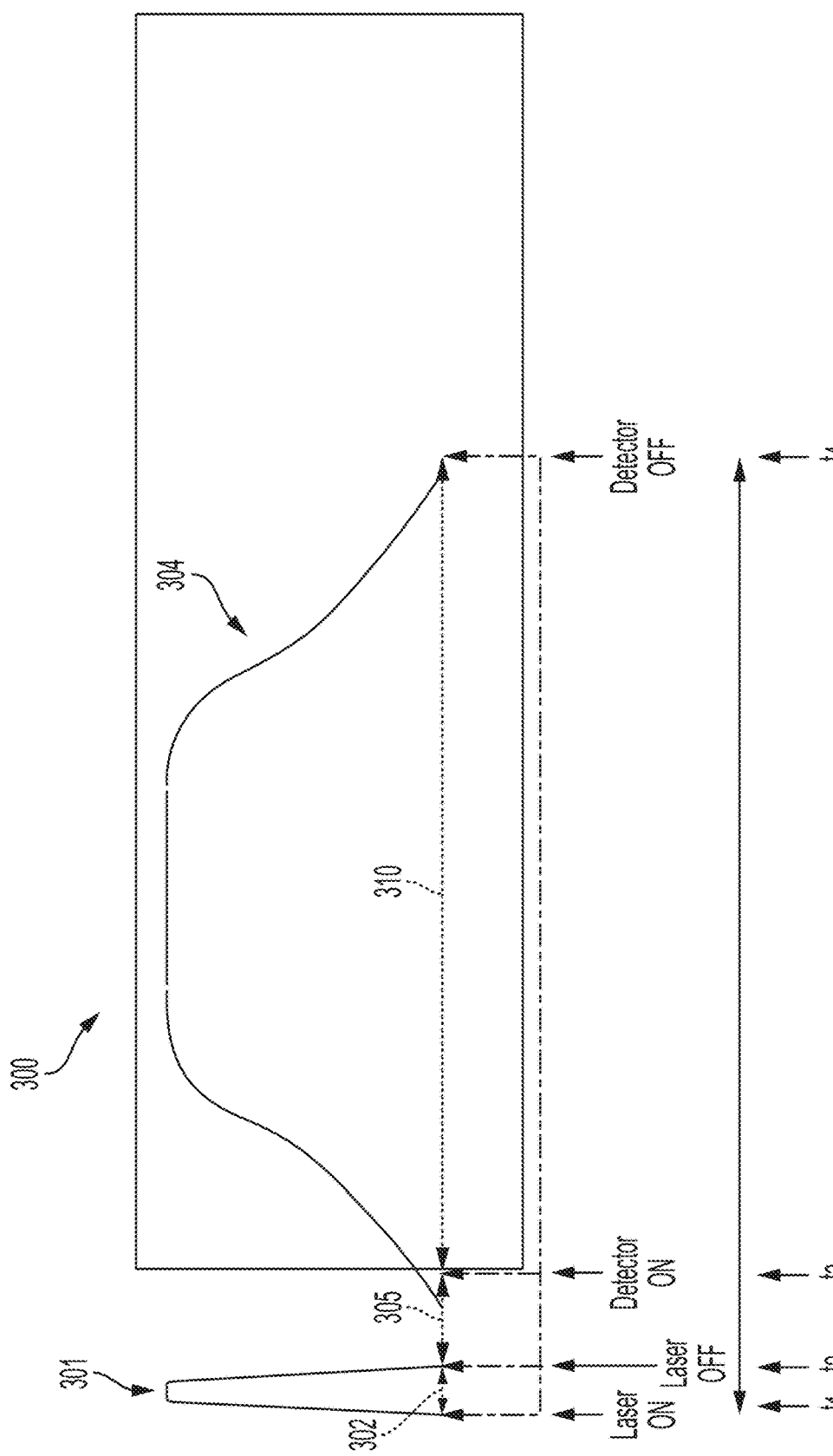
FIG. 3 illustrates a diagram showing time gated excitation and delayed detection according to embodiments of the present invention.

FIG. 3 illustrates a diagram 300 showing time gated excitation by the laser and delayed detection by the detector according to embodiments of the present invention. The laser is turned on to transmit a laser pulse 301 at time $t_1$. The duration of the laser pulse 301, or the pulse width 302 of the laser beam extends between time $t_1$ and time $t_2$. According to one or more embodiments of the present invention, the pulse width 302 of the laser beam is about 25 to about 100 picoseconds (ps).

Between time $t_2$ and time $t_3$, the laser beam is off, and there is no transmission of a laser pulse 301. According to some embodiments of the present invention, the time delay 305 between time $t_2$ and time $t_3$ is about 1-10 ns to about 10-50 ns. The detector is initially in the off state for as long as the laser pulse 301 is emitted, between time $t_1$ and time $t_2$. The detector is further maintained in the off state between time $t_2$ and time $t_3$. The detector remains in the off state so as not to receive reflections of the entire laser pulse, including the end portion of the pulse, or from other objects in proximity. The detector is therefore in an off state between $t_1$ and $t_3$. Detection by the detector occurs after the laser that emits the excitation laser pulse has been deactivated.

At time $t_3$, the detector is activated (turned on) and begins receiving reflections. The detector remains in the on state until time $t_4$ when it is turned off. The time the detector is in an on state, extends from time $t_3$ to time $t_4$. The detector therefore only acquires reflections from the target sample fluorescence emission 304. According to one or more embodiments of the present invention, the detector integration time between time $t_3$ and time $t_4$ is about 1 to about 10 milliseconds (ms). The camera is triggered a few nanoseconds after the excitation pule event. The subsequent integration of the camera image can be much longer than the fluorescence lifetime of the emission, which is typically hundreds of nanoseconds, and is commensurate with the frame rate of the camera.

The detector integration time captures emission lifetimes 310, for example having tens of nanoseconds, with the time-delayed detector without the need for spectral filters. So long as the system is sealed from outside light pollution, the systems and methods enable detection of tens of photons, which enables single bio-agent detection without the need for PCR amplification.

According to some embodiments of the present invention, the detector is capable of single photon counting sensitivity and features millisecond integration times. Each "frame" can acquire about 100 nanosecond (ns) fluorescence emission, and multiple frame or capture events can still be employed for enhanced signal-to-noise.

Figure 4A:
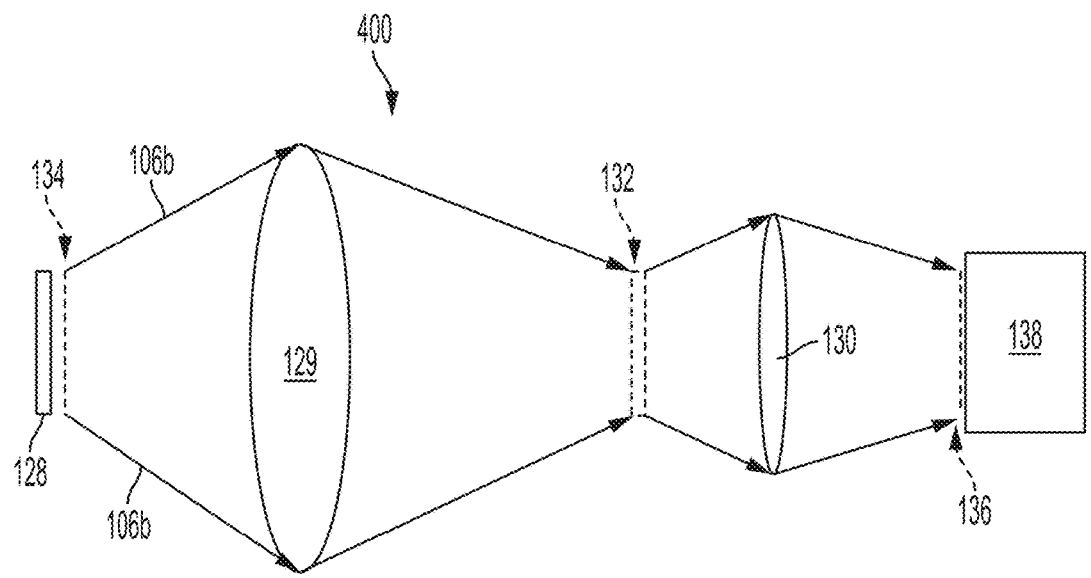
FIG. 4A illustrates a diagram of a pupil plane detector layout according to embodiments of the present invention.

FIG. 4A illustrates a diagram of a pupil plane detector layout 400 according to embodiments of the present invention. The reflected fluorescent light 106b passes through the filter 128 arranged behind the pupil entrance 134. The fluorescent light 106b then enters objective lens 129 that collects the reflected laser light from the pupil plane entrance and focuses an image of the target sample at its focal point 132. A field stop (not shown) can be arranged at a distance away from the objective lens 129 that is equivalent to the focal length $f_1$ of the objective lens 129, at the focal point. The field stop can minimize the amount of stray light from around the target that is collected into the imaged signals. From this focused point, the light then diverges and is collected by reimaging optical lens 130. Reimaging optical lens 130 is illustrated as a single lens positioned a distance away from the focal point 132 equivalent to the lens's focal length $f_2$. However, the reimaging optical lens 130 need not be composed of a single lens, but instead can include a combination of lenses and/or optical elements. The output of the reimaging optical lens 130 is sent to the signal detector 138 at the pupil plane 136 as an inverted and de-magnified image of the light entering the pupil of the objective lens 129. Utilizing the described optical relay system enables collection of all the emitted photons from the target sample 118.

Because the detector 138 is imaging the light entering the pupil itself, instead of the focused image of the target spot (at the focal length $f_1$ from the objective lens 129), this configuration is employing what is referred to as a "pupil plane imaging." Placing the camera in the pupil plane ensures all photons are captured and pixels can be integrated, since not imaging, for a significant signal-to-noise ratio. The spatially integrated detection arrangement enables high sensitivity detection of fluorescently tagged biological agents, for example, with numbers less than one hundred in some embodiments of the present invention, which eliminates the need for wet chemistry PCR amplification processes or spectral band filters. The systems and methods described herein do not include spectral band fibers or require PCR amplification.

Figure 4B:
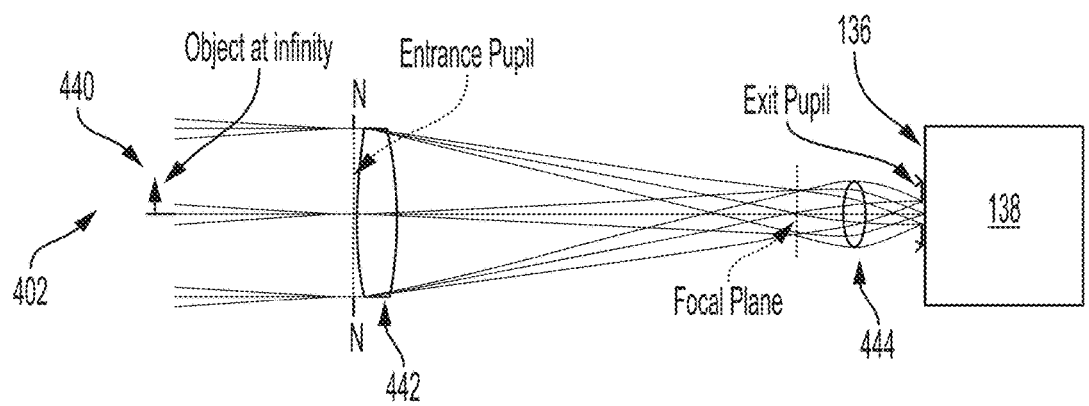
FIG. 4B illustrates a diagram illustrating pupil plane imaging according to embodiments of the present invention.

FIG. 4B illustrates another diagram illustrating pupil plane imaging 402 according to embodiments of the present invention. An object 440 is imaged as light reflected from the image passes through an objective lens 442 arranged in front of the pupil entrance. The reflected light is focused at the focal plane and diverges through a reimaging optical lens that collects the light. The output of the reimaging optical lens 444 is sent to the detector 138 arranged at the pupil plane 136.

Figure 5:
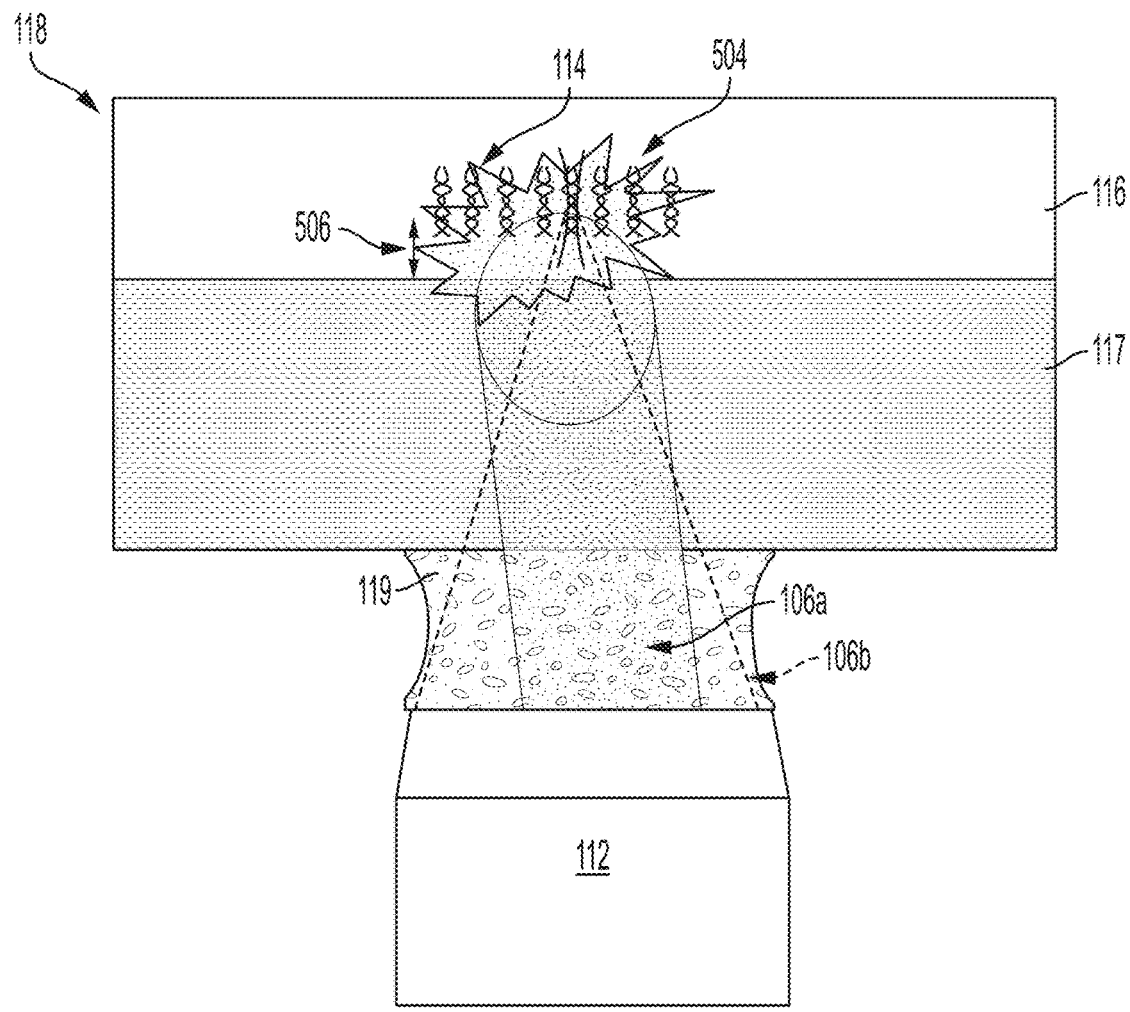
FIG. 5 illustrates an enlarged view of an excited sample according to embodiments of the present invention.

FIG. 5 illustrates an enlarged view of an excited sample according to embodiments of the present invention. The excitation beam 106a passes through microscope objective lens 112 to the target sample 118. The microscope objective lens 112 is a TIR objective lens. TIR microscopes enable observation of a thin region of the target sample 118.

The sample 504 is a biological sample according to one or more embodiments of the present invention. Although, sample 508 is not limited to biological samples and can be any material, composition, or compound. The sample 508 is labeled with a fluorescent tag (a fluorophore) that emits fluorescent light 520 according to some embodiments of the present invention. Yet, according to other embodiments of the present invention, the sample 508 includes an inherent fluorophore.

The sample 504 is a nucleic acid sample, such as DNA, RNA, or a combination thereof. In the embodiments shown in FIG. 5, the sample 504 is DNA labeled with a fluorescent tag. In other embodiments, the sample 504 is denatured DNA fragments.

Examples of fluorescent tags include, but are not limited to, 9-diethylamino-5-benzo[a]phenoxazinone (Nile Red), cyanin (e.g., Cy3, Cy5, or Cy7), Indocyanine green (IR125), Alexa Fluor 750 dye, fluorescein, 5-carboxytetramethylrhodamine (5-TAMRA), sulforhodamine 101 acid chloride (Texas Red), or Atto740. Other non-limiting examples of fluorescent tags include quantum dots, such as CdS, CdSe, and CdTe.

According to exemplary embodiments of the present invention, the length of the DNA samples are about 100 to about 200 base pairs long, with a length of about 25 to about 50 nanometers (nm).

Various isolation methods can be used to isolate the biological sample, such as DNA fragments, from a sample such as whole blood. According to one or more embodiments of the present invention, dielectrophoretic isolation is used to separate DNA biomarkers from blood and plasma, which is then analyzed using the described methods and systems.

The sample 504 is in an aqueous solution layer 116 that is arranged on a cover slip 117. The aqueous solution layer 116 includes a water-based chemistry with additional components that vary depending on the type of sample 504. According to some embodiments of the present invention, the aqueous solution layer 116 has a refractive index of about 1.33 to about 1.4.

The coverslip 117 includes glass. According to some embodiments of the present invention, the cover slip has an index of about 1.516. The aqueous solution layer 116 has a lower refractive index than the coverslip 117.

An oil 119 is arranged between the coverslip 117 and the objective lens 112 and has an index that matches the index of the cover slip 117. A non-limiting example of a suitable oil 119 includes Cedar tree oil.

TIR microscopy allows for selective excitation of the surface-bound fluorophores 114 in the sample 504 within a thin region of the sample 504, while non-bound molecules are not excited and do not fluoresce. Elimination of background fluorescence from outside the focal plane improves signal-to-noise ratio, and consequently, spatial resolution of the features of interest. TIR microscopy uses the unique properties of an induced evanescent wave in a limited specimen region immediately adjacent to the interface between two media having different refractive indices, in this example, between the coverslip 117 and the aqueous solution layer 116, having an index of about 1.33 to about 1.4.

As the excitation beam 106a, which is an evanescent wave, encounters the interface between the coverslip 117 and the aqueous solution layer 116, which have different indices, a portion or all of the light is confined to the higher index medium, which is the coverslip 117. When the excitation beam 106a is incident at angles greater than the critical angle, the reflected light generates a highly restricted electromagnetic field adjacent to the interface, in the lower-index medium, or in the aqueous solution layer 116. Therefore, fluorophores 114 located in the vicinity of the interface of the cover slip 117 and aqueous solution layer 116 can be excited by the evanescent field, provided they have potential electronic transitions at energies within or very near the wavelength bandwidth of the illuminating beam. Because of the exponential falloff of evanescent field intensity, the excitation of fluorophores 114 in the sample 504 is restricted to a thin region of the aqueous solution layer 116. Because excitation of fluorophores 114 in the bulk of the specimen is avoided, confining the secondary fluorescence emission to a very thin region, a much higher signal-to-noise ratio is achieved compared to conventional wide-field epifluorescence illumination. This enhanced signal level makes it possible to detect single-molecule fluorescence.

According to exemplary embodiments of the present invention, sample 504 is arranged about 75 to about 125 nm from the interface of the coverslip 117 and the aqueous solution layer 116, and the depth of focus of the excitation beam 106a is about 100 to about 300 nm. The fluorophore 114 in the sample 504 is excited by the excitation beam 106a in the thin region of the aqueous layer 116 and emits fluorescent light (fluorescent light 106b) back through the objective lens 112.

Figure 6:
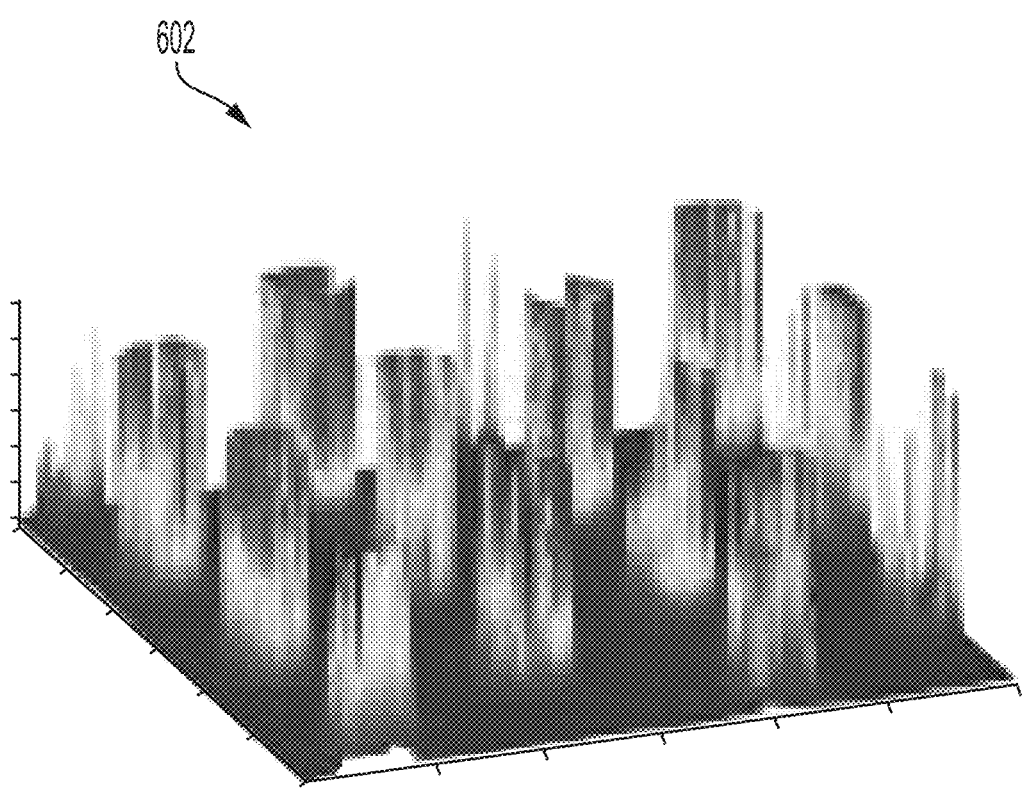
FIG. 6 illustrates a three-dimensional (3D) fluorescence intensity image obtained using conventional methods.

Conventional imaging includes a focal plane imaging approach, or a non-pupil plane approach, in which a conventional camera port in a microscope is used to image fluorescently tagged samples. Yet, in accordance with embodiments of the present invention, the "standard" spatially resolved signal display used in conventional focal plane (FP) imaging mode is replaced with a cumulative spatially integrated signal without spatial resolution, but with added signal to noise ratio (SNR) enhancement due to the spatial averaging/signal addition. FIG. 6 illustrates a conventional three-dimensional (3D) fluorescence intensity image 602 obtained using focal plane imaging. The image 602 was obtained by imaging based sensing, where the focal plane array (FPA) or sensor spatially resolves the two-dimensional (2D) sample array that has activated localized areas where fluorophore tagged biological agents are located or immobilized, which looks like an intensity based histogram. The pixels commensurate with the signal detection peaks will exhibit pixel-level noise and associated SNR. In contrast, according to embodiments of the present invention, spatially averaging the entire signal area by placing the FPA sensor camera in the pupil plane, which no longer resulted in a spatially resolved 2D image with intensity map, will provide a single cumulative signal, which results in a pixel-averaged noise or SNR performance with much higher SNR than the single pixel performance.

The above described systems and methods can be used in a variety of applications. According to exemplary embodiments, the sample 504 includes DNA fragments isolated from a sample of blood. Cell-free DNA fragments have been correlated with various disease states, for example metastatic cancer. DNA fragments can also be evaluated as markers for various clinical pathologies, including cell death or stress, trauma, infection, autoimmune disorders, and cardiovascular disease. The excitation and detection systems disclosed herein can be packaged as portable, field deployable systems, as they do not require PCR amplification for detection.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

While the preferred embodiments to the invention have been described, it will be understood that those skilled in the art, both now and in the future, may make various improvements and enhancements which fall within the scope of the claims which follow. These claims should be construed to maintain the proper protection for the invention first described.

What is claimed is:

1. A system for imaging a biological target, comprising:
   a light excitation source providing an excitation laser pulse;
   an objective lens that receives reflections of the excitation laser pulse;
   a reimaging optical lens that generates an image of an entrance pupil of the objective lens; and
   a time-delayed detector that detects the image of the entrance pupil.

2. The system of claim 1, wherein the objective lens, the reimaging optical lens, and the detector are enclosed in a housing.

3. The system of claim 1, wherein the system does not include a spectral band filter.

4. The system of claim 1, wherein the detector is a complementary metal oxide semiconductor camera.

5. The system of claim 1, wherein the time-delayed detector comprises a shutter.

6. The system of claim 1 further comprising a controller that activates the time-delayed detector after the light excitation source has been deactivated.

7. A system for imaging a biological target, comprising:
   a light excitation source providing an excitation laser pulse;
   a total internal reflectance microscope objective lens;
   an objective lens that receives reflections of the excitation laser pulse;
   a reimaging optical lens that generates an image of an entrance pupil of the objective lens; and
   a time-delayed detector that detects the image of the entrance pupil.

8. The system of claim 7, wherein the objective lens, the reimaging optical lens, and the detector are enclosed in a housing.

9. The system of claim 7, wherein the system does not include a spectral band filter.

10. The system of claim 7, wherein the detector is a complementary metal oxide semiconductor camera.

11. The system of claim 7, wherein the time-delayed detector comprises a shutter.

12. The system of claim 7 further comprising a controller that activates the time-delayed detector after the light excitation source has been deactivated.

13. A method for imaging a biological target, the method comprising:
   providing an excitation laser pulse to the biological target;
   receiving, by an objective lens, reflections of the excitation laser pulse from the biological target;
   generating an image, by a reimaging optical lens, of an entrance pupil image of the objective lens; and
   detecting by a detector, following a time delay, the entrance pupil image.

14. The method of claim 13, wherein the objective lens, the reimaging optical lens, and the detector are encased in a housing.

15. The method of claim 13, wherein the method does not include using a spectral band filter.

16. The method of claim 13, wherein the detector is a complementary metal oxide semiconductor camera.

17. The method of claim 13, wherein the detector comprises a shutter.

18. The method of claim 13, wherein detecting by the detector occurs after a light source that emits the excitation laser pulse has been deactivated.

19. The method of claim 13, wherein the biological target comprises deoxyribonucleic acid.

20. The method of claim 13, wherein providing the excitation laser pulse is through a total internal reflectance microscope objective lens.

* * * * *